United States Patent
Peterson et al.

(10) Patent No.: US 11,351,028 B2
(45) Date of Patent: Jun. 7, 2022

(54) STENT LOADING DEVICE WITH FLUID RESERVOIR

(71) Applicant: 4C Medical Technologies, Inc., Brooklyn Park, MN (US)

(72) Inventors: Alex A. Peterson, Brooklyn Park, MN (US); Jason S. Diedering, Minneapolis, MN (US); Saravana B. Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 111 days.

(21) Appl. No.: 16/558,897

(22) Filed: Sep. 3, 2019

(65) Prior Publication Data

US 2020/0069423 A1 Mar. 5, 2020

Related U.S. Application Data

(60) Provisional application No. 62/726,614, filed on Sep. 4, 2018.

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/9525* (2020.05); *A61F 2250/0058* (2013.01)

(58) Field of Classification Search
CPC ............. A61F 2/95; A61F 2/24; A61F 2/2466
(Continued)

(56) References Cited

U.S. PATENT DOCUMENTS 8,109,995 B2 * 2/2012 Paniagua ............... A61F 2/2436
623/2.14
8,246,677 B2 * 8/2012 Ryan ..................... A61F 2/2409
623/1.26
(Continued)

OTHER PUBLICATIONS

International Search Report and Written Opinion, dated Oct. 29, 2019, for PCT Application No. PCT/US2019/049412, filed Sep. 4, 2019.
(Continued)

*Primary Examiner* — Suzette J Gherbi
(74) *Attorney, Agent, or Firm* — Barnes & Thornburg LLP; Jeffrey R. Stone (57) ABSTRACT

A device and method for predictably and controlling the collapsing of a collapsible and expandable stent for subsequent translation through a delivery sheath lumen to an anatomical target such as a heart valve or intravascular location for expansion and implantation. The loading device defines in inner lumen comprising a successively decreasing, from the proximal to the distal direction, inner diameter alternating between two sections of decreasing diameter and two sections of constant diameter until reaching the inner diameter of the delivery sheath. A fluid-filled reservoir is provided at the proximal end of the loading device that is configured to provide moisture or wetting for materials associated with or attached to the stent that require moisture retention. Thus, as the stent is being collapsed with the loading device, at least a portion of the stent may be immersed in the fluid reservoir to preserve the subject material.

14 Claims, 5 Drawing Sheets

(58) Field of Classification Search
USPC .......................................................... 623/2.1
See application file for complete search history.

(56) References Cited

U.S. PATENT DOCUMENTS

| | | | | |
|---|---|---|---|---|
| 8,518,106 | B2* | 8/2013 | Duffy | A61F 2/966 623/2.11 |
| 8,790,396 | B2* | 7/2014 | Bergheim | A61F 2/2427 623/2.11 |
| 9,326,853 | B2* | 5/2016 | Olson | A61F 2/243 |
| 9,795,477 | B2* | 10/2017 | Tran | A61F 2/958 |
| 2014/0222140 | A1 | 8/2014 | Schreck | |
| 2015/0290007 | A1* | 10/2015 | Aggerholm | A61F 2/962 623/1.11 |
| 2015/0366690 | A1* | 12/2015 | Lumauig | A61F 2/966 623/1.11 |
| 2016/0235532 | A1* | 8/2016 | Tran | A61F 2/958 |
| 2017/0252191 | A1 | 9/2017 | Pacetti | |
| 2020/0069449 | A1* | 3/2020 | Diedering | A61F 2/2436 |
| 2020/0323668 | A1* | 10/2020 | Diedering | A61F 2/2436 |
| 2020/0337765 | A1* | 10/2020 | Smith | A61M 25/0147 |
| 2020/0375733 | A1* | 12/2020 | Diedering | A61F 2/2427 |

OTHER PUBLICATIONS

Notification Concerning Transmittal of International Preliminary Report on Patentability and International Preliminary Report on Patentability issued in PCTUS2019/049412, dated Mar. 18, 2021.

* cited by examiner

STENT LOADING DEVICE WITH FLUID RESERVOIR

CROSS-REFERENCE TO RELATED APPLICATIONS

This application claims the benefit of U.S. Provisional Application Ser. No. 62/726,614, filed Sep. 4, 2018 and entitled STENT LOADING DEVICE WITH FLUID RESERVOIR, the entire contents of which are incorporated herein by reference.

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber. More specifically, the invention relates to devices configured to load a stent, e.g., a prosthetic heart valve frame, into a lumen of a delivery sheath or catheter for translation through the lumen to the distal end of the delivery sheath or catheter.

Description of the Related Art

Stents in general, and prosthetic cardiac valve and left atrial appendage occluding devices specifically, are well known in the art. The native heart valves, e.g., aortic, pulmonary, tricuspid and mitral valves, are critical in assuring the forward-only flow of an adequate supply of blood through the cardiovascular system. These heart valves may lose functionality as a result of, inter alia, congenital, inflammatory, infectious diseases or conditions. Early interventions repaired or replaced the dysfunctional valve(s) during open heart surgery. More recently, besides the open heart surgical approach discussed above, gaining access to the valve of interest may be achieved percutaneously via one of at least the following known access routes: transapical; transfemoral; transatrial; and trans septal delivery techniques, collectively transcatheter techniques.

Generally, in a transcatheter technique, the prosthetic valve is mounted within a stented frame that is capable of achieving collapsed and expanded states. The device is collapsed and advanced through a sheath or delivery catheter positioned in a blood vessel of the patient until reaching the implantation site. The stented frame is generally released from the catheter or sheath and, by a variety of means, expanded with the valve to the expanded functional size and orientation within the heart. One of the key issues is ease of delivery of the prosthetic valve, including the stent frame and valve. More specifically the outer diameter of the collapsed device within the catheter is of significant interest. The present invention addresses this issue.

DESCRIPTION OF THE RELATED ART

Figure 1:
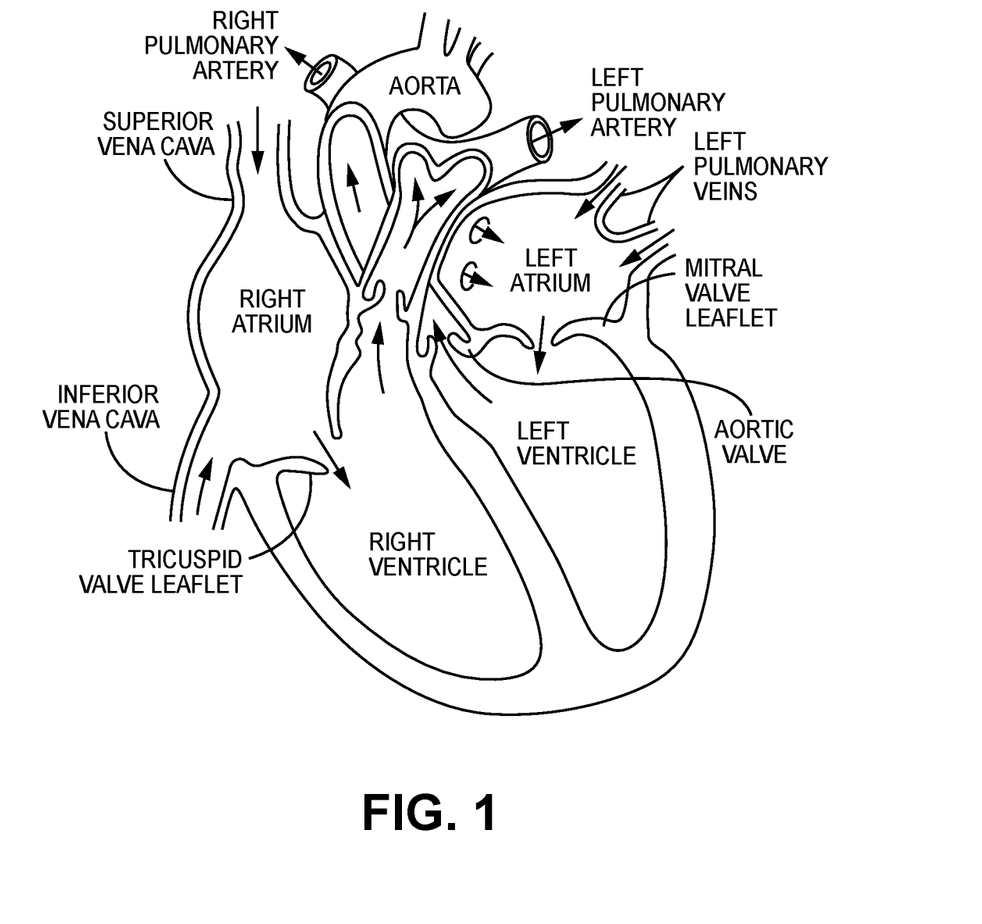
FIG. 1 illustrates certain features of the heart in cross-section.

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and trans septal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, known "replacement" prosthetic heart valves are intended for full replacement of the native heart valve. Therefore, these replacement heart valves physically engage tissue within the annular throat, i.e., below the annular plane and upper annular surface, and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as an adjunctive and/or supplementary functional valve as well as be fully capable of replacing the native function of a valve that has lost, or will lose, most or all of its functionality. However, the inventive solutions described infra will apply generally to all types and forms of heart valve devices, unless otherwise specified. The present disclosure also applies, as the skilled artisan will recognize, to stents generally.

Further, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the native annulus or annular throat) connected from the stent device down through the annular throat, with the sub-annular surface within the left ventricle, the left ventricular chordae tendineae and even into the left ventricle wall surface(s). See, e.g., the MitraClip® marketed by the Abbott Group and currently the only US approved repair device. With the MitraClip® a catheter containing the MitraClip® is inserted into the femoral vein. The device enters the heart through the inferior vena cava to the right atrium and delivered transseptally. The MitraClip® passes through the annulus into the left ventricle and sits below the leaflets, clipping the leaflets to decrease regurgitation.

Such 2-chamber and native annulus solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the native annulus and/or annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, some of the embodiments, or portions thereof, described herein are readily applicable to single or 2-chamber solutions, unless otherwise indicated.

Finally, known prosthetic cardiac valves consist of two or three leaflets that are arranged to act as a one-way valve, permitting fluid flow therethrough in the antegrade direction while preventing retrograde flow. The native mitral valve is located retrosternally at the fourth costal cartilage, consisting of an anterior and posterior leaflet, chordae tendinae, papillary muscles, ventricular wall and annulus connected to the atria. Each native leaflet is supported by chordae tendinae that are attached to papillary muscles which become taut with each ventricular contraction preserving valvular competence. Both the anterior and posterior leaflets of the native valve are attached via primary, secondary and tertiary chordae to both the antero-lateral and posterio-medial papillary muscles. A disruption in either papillary muscle in the setting of myocardial injury, can result in dysfunction of either the anterior or posterior leaflet of the mitral valve. Other mechanisms may result in failure of one, or both of the native mitral leaflets. In the case of a single mitral valve leaflet failure, the regurgitation may take the form of a non-central, eccentric jet of blood back into the left atrium. Other leaflet failures may comprise a more centralized regurgitation jet. Known prosthetic valve replacements generally comprise leaflets which are arranged to mimic the native valve structure, which may over time become susceptible to similar regurgitation outcomes.

The applications for collapsible and expandable stents are not limited to prosthetic heart valve implants. Vascular stents are commonly used and are generally collapsible to facilitate delivery through the lumen of a delivery catheter to the working site where the stent is translated out of the lumen of the catheter and it is expanded, either by a self-expanding means or through an expanding mechanism such as, inter alia, an expandable balloon.

As discussed above, known delivery methods and devices comprise expandable prosthetic valve stents and vascular stents that are collapsed during delivery via a delivery catheter. The problems with such collapsing and expanding structures include placing strain on the regions of the structure, e.g., stent, that must bend to accommodate the collapsing and expanding states. Further, the collapsed geometry in known devices may not be controlled or predictable, adding to the strain on the collapsing and expanding structure elements. Thus, the structures and methods for achieving the collapsed state within the delivery catheter or sheath lumen must allow predictable and repeatable collapsing to maintain and retain the integrity of the collapsing structure. Moreover, the stent, e.g., prosthetic heart valve or vascular stent, may comprise biological and/or biologically compatible material that cannot be allowed to become dry. Therefore, retaining a fluid reservoir within which the subject stent may reside is critical.

Various embodiments of the present invention address these, inter alia, issues.

BRIEF SUMMARY OF THE INVENTION

A device and method for predictably and controlling the collapsing of a collapsible and expandable stent for subsequent translation through a delivery sheath lumen to an anatomical target such as a heart valve or intravascular location for expansion and implantation. The loading device defines in inner lumen comprising a successively decreasing, from the proximal to the distal direction, inner diameter alternating between decreasing diameter and constant diameter until reaching the inner diameter of the delivery sheath. There are at least two sections of decreasing diameter and at least two sections of constant diameter. A fluid-filled reservoir is provided at the proximal end of the loading device that is configured to provide moisture or wetting for materials associated with or attached to the stent that require moisture retention. Thus, as the stent is being collapsed with the loading device, at least a portion of the stent may be immersed in the fluid reservoir to preserve the subject material.

DETAILED DESCRIPTION OF THE INVENTION

Generally, various embodiments of the present invention are directed to devices and methods for achieving a predictable collapsed configuration or state for a collapsible and expandable support structure or stent as well as providing a mechanism for ensuring moisture retention within biological materials that may be attached or otherwise integrated with the collapsible and expandable support structure during the collapsing step.

The support structure or stent has multiple functions to aid with the treatment of cardiac valve regurgitation (mitral or tricuspid). These functions include its function as a scaffold for the functioning 4C valve, apposition to the atrial anatomy, optimized radial force for compliance with atrial distension, ability to load and deploy from a minimally invasive delivery system, and geometry to support with mitigating against paravalvular leak (PVL). The design features of the stent are adapted to meet one or more of the functions identified above. Specific design features and attributes for exemplary stents are discussed in detail below to assist in understanding of the utility of the funneling loading device and related methods. As discussed above, the invention is not limited to prosthetic heart valves comprising stent support structures, but may also be applied to collapsible and expandable stents such as commonly used for intravascular procedures.

Certain exemplary embodiment stent design concepts are intended to support minimally invasive procedures for the treatment of valvular regurgitation—mitral, tricuspid and/or otherwise. The stents may be self-expandable (e.g. nitinol or similar materials) or balloon expandable (e.g. cobalt chromium or similar materials). The stents are typically made of cells that may be open celled diamond like structures or continuous structures that have a working cell element. The stents may also be constructed using tubing, wires, braids or similar structures. Specific design features that aid with the functioning of the stent are described in detail below.

Stent "Iris" Transition Cells

Figure 2:
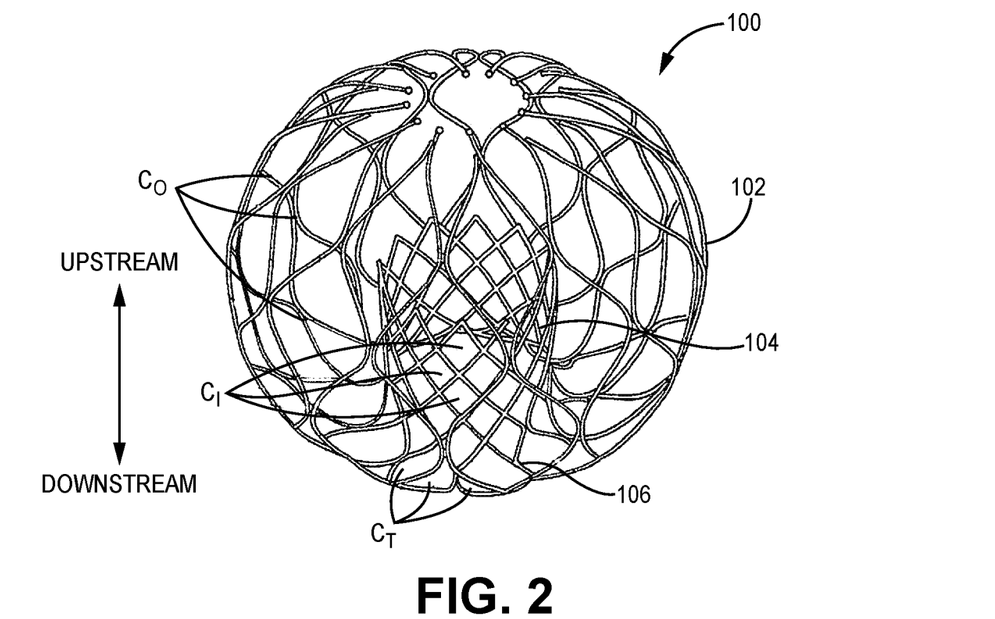
FIG. 2 illustrates a perspective view of an exemplary stent.
Figure 3A:
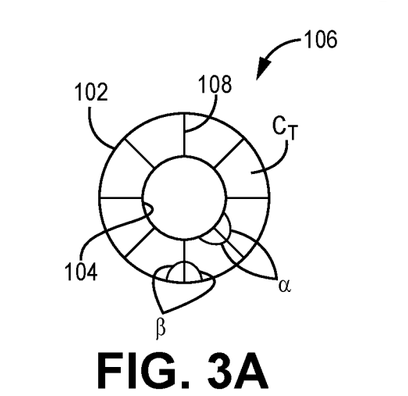
FIG. 3A illustrates a bottom view of one embodiment of a transition section of the exemplary stent of FIG. 2.
Figure 3B:
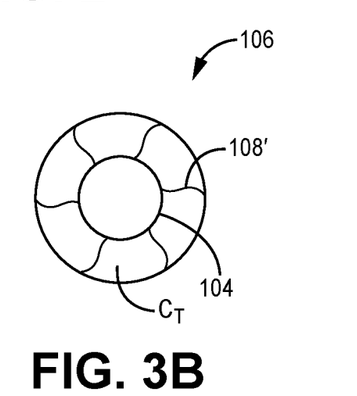
FIG. 3B illustrates a bottom view of one embodiment of a transition section of the exemplary stent of FIG. 2.

With reference now to FIGS. 2-3B, one embodiment of the stent 100 of the present invention comprises an outer section 102—that may generally be circular though need not be a perfectly round circular structure when fully and/or partially expanded—and an inner valve support section 104—which may be cylindrical but need not be a constant diameter cylinder and is adapted to support and retain prosthetic valve leaflets (not shown in FIG. 2) within the inner valve support section 104, most preferably at a point that located above the native annulus, e.g., the mitral valve annulus, though other attachment points for the prosthetic leaflets are within the scope of the present invention. Further, as discussed above, the stent 100 may be configured to supplement and/or replace the function of the tricuspid valve. A preferred construction comprises the prosthetic leaflets disposed above the native leaflets, wherein the prosthetic leaflets are attached and spaced sufficiently away from (above) the native leaflets so as to not physically interfere or interact with the native leaflets. However, certain embodiments contemplate some interaction with the native leaflets.

Individual cells $C_O$ forming the outer section 102 of stent 100 are visible in FIG. 2 as open cell regions defined by the material used to form the expandable stent 100.

Individual cells $C_I$ forming the inner valve support section 104 are also illustrated as open cells regions formed within an inner region R defined by outer section 102, wherein the inner valve support section extends radially upward into the inner region R. As shown, individual cells $C_I$ are of a different size, and may comprise a different shape, than that of individual cells $C_O$.

The region of stent 100 that facilitates the radially inward transition of the stent 100 from the outer section 102 to the inner section 104 of the stent 100 is the transition cell region 106. Transition cell region 106 may comprise cells $C_T$ that may comprise a different size and/or shape that either the outer section cells $C_O$ and/or the inner section cells $C_I$. The outer and/or inner regions 102, 104, and/or transition cell region 106 of the stent 100 may be constructed from one continuous structure or may combine two or more structures to achieve intended design goals. Transition cell region 106 comprises generally a radially upward turn to allow the inner valve support section 104 to reside within the inner region 102 as shown in FIG. 2. In some embodiments, the lower portion of inner valve support section 104, that is the portion of the inner valve support section 104 that is in connection with the cells $C_T$ of transition cell region 106 may also comprise a curving shape to facilitate and/or complete the radially upward turn into the inner region 102.

The geometry and/or shape of the transition cells $C_T$ may be substantially straight segments when expanded as in FIG. 3A below or may, as shown in FIG. 3B, incorporate an offset or a twist in the stent cell pattern when expanded to allow for a controlled compression of the stent. Exemplary cross-sectional geometry of the transition cell region 106 viewed from the bottom of stent 100 is represented schematically in FIGS. 3A and 3B.

This transition cell region 106 of the stent 100 may be a strut, completed cell section or a partial cell section. The transition cell region 106 may have any number of struts (minimum of 3) or cell sections as generally required to meet design needs. Transition cells $C_T$ or struts may be evenly spaced and formed by substantially straight and equally spaced apart struts 108 as shown in FIG. 3A, that extend away from the inner valve support section 104 with equal angles α on both sides of the strut 108 and equal angles β on both sides of strut 108 with respect to its intersection or integration with outer support section 102.

Figure 3C:
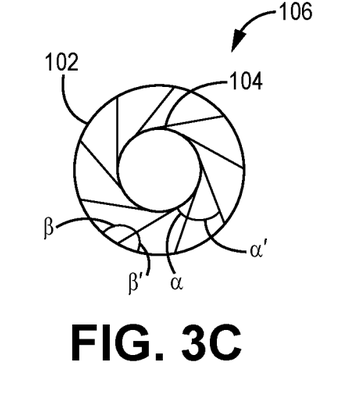
FIG. 3C illustrates a bottom view of one embodiment of a transition section of the exemplary stent of FIG. 2.

In a preferred embodiment, the struts 108 of transition section 106 may be straight as in FIG. 3A, but with non-equal angles relative to the inner valve support section 104 and outer support section 102 as shown in FIG. 3C. There, the straight struts 108 are slanted so that a smaller angle α and a larger angle α' are provided relative to the inner valve support section 104. Similarly, a smaller angle β' and a larger angle β are provided relative to the outer support section 102. This allows a compressed nesting of the slanted struts 108 of transition section 106.

In another preferred embodiment, the transition cell region 106 may comprise transition cell struts 108' that comprise transition cells CT that are formed by struts 108' having an offset, i.e., not straight, are twisted and/or curvilinear. The degree of offset and/or twist and/or curvature of the struts 108', and therefore the size and/or shape of the resultant expanded cells CT may be varied dependent on the number of cells/struts in the transition cell region 106, packing density when the stent is collapsed, and stress/strain distribution limitations of the transition cell region 106.

Figure 4A:
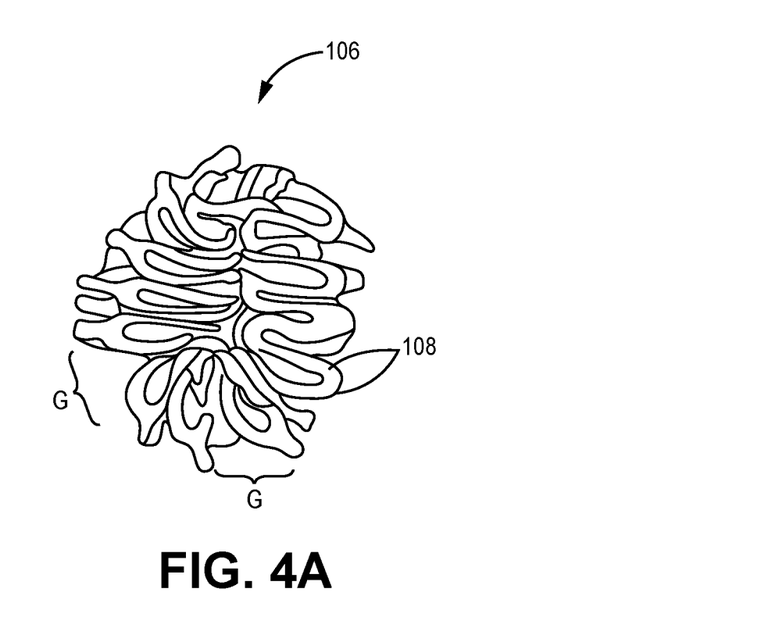
FIG. 4A illustrates a bottom view of one embodiment of a collapsed transition section of the exemplary stent of FIG. 2.

The structure of FIGS. 3B and 3C are preferred over the straight transition cell region 106 structure of FIG. 3A for several reasons. FIG. 4A shows a transition cell region 106 in a collapsed form using the substantially straight struts 108 of FIG. 3A and with, undesirable, gaps G between selected struts 108. Though this resultant gapping collapsed transitional cell region 106 is workable, it is not optimal.

Figure 4B:
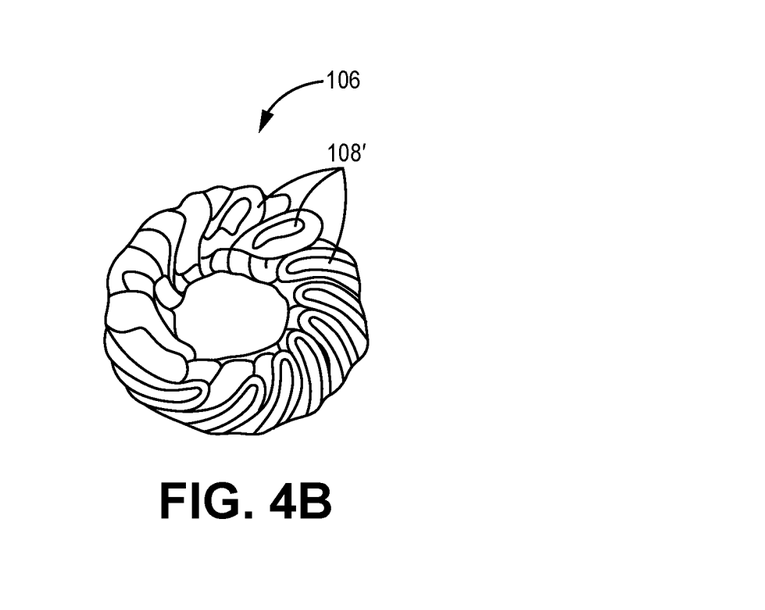
FIG. 4B illustrates a bottom view of one embodiment of a collapsed transition section of the exemplary stent of FIG. 2.

Thus, the transition section 106 of FIG. 4B, using e.g., the offset and/or twisted and/or curved plurality of struts 108' of FIG. 3B or the slanted straight struts 108 of FIG. 3C, allows for a controlled and predictable collapsed form of the stent, without gapping between the struts 108'. This, in turn, minimizes the amount of stress/strain concentration at the lower region of the stent 100 during collapsing as is required for delivery of the expandable stent 100 to the heart region of interest. Additionally, the collapse of the cells is also symmetrical and uniform, which could aid with mitigating against damage to the valve tissue or fabric when it is attached to the stent cells. Reduction in overall stress/strain of the transition strut section may benefit the durability of the stent and the valve tissue.

A feature of certain embodiments of the transition cell region 106 as shown in FIGS. 3B and 3C and 4B, i.e., with offset, twisted and/or curved struts 108' or slanted straight struts 108, is that, as best shown in FIG. 3B, the struts 108' each comprise the same offset, twist and/or curvature. This, in turn, enables a close nesting of adjacent struts 108' as the stent 100 is collapsed down for delivery and subsequent expansion.

Thus, as the stent is collapsed for loading into a delivery system, the transition section design allows for a controlled compression of the stent, and reduces the stress concentration on the stent cells. of the transition strut section may benefit the durability of the stent and the valve tissue.

As the skilled artisan will now recognize from the above, the geometry of the exemplary stent's struts enables a transition from expanded to collapsed.

Figure 5:
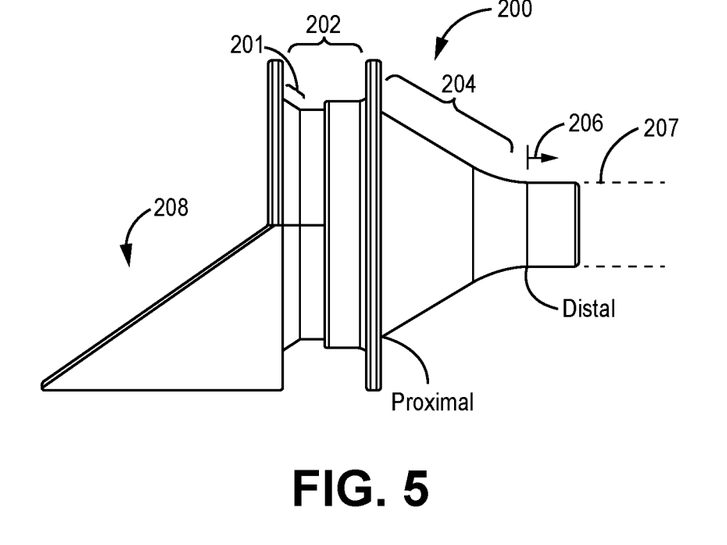
FIG. 5 illustrates a side broken away view of one embodiment of the present invention.
Figure 6:
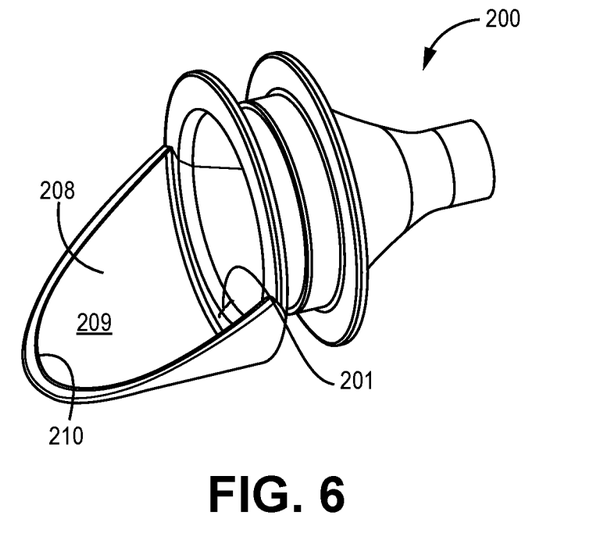
FIG. 6 illustrates a perspective view of one embodiment of the present invention.

FIGS. 5 and 6 illustrate an exemplary loading device 200 that may initiate the transition of the exemplary stent, as well as other collapsible and expandable support structure stents, from expanded to collapsed, wherein the collapsed state or configuration is prepared and sufficient for translation into and along the delivery catheter or sheath to the targeted anatomical location.

Thus, stent loading device 200 is comprising a proximal transition section 201 of decreasing diameter from proximal to distal in fluid communication with a substantially cylindrical proximal section of constant diameter 202 that transitions to a decreasing diameter section 204 that, in turn, transitions to a distal constant diameter section 206. The decreasing diameter section 204 is illustrated as a conical shape, but various embodiments may comprise a curvilinear and or concave profile. In each case, the dimensional requirement is that the inner diameter of the decreasing diameter section 204 provides a substantially smoothly transitioning decreasing diameter from the substantially cylindrical constant diameter section 202 to the distal constant diameter section 206 which is, in turn, operatively attached and in fluid communication with a proximal end of a delivery sheath 207, wherein proximal means the portion of the delivery sheath 207 located outside the patient's body. It will be readily understood that a lumen is defined within loading device 200 that is, at constant diameter section 206, will be substantially the same diameter as the lumen of delivery sheath 207 to provide a smooth transition therebetween during translation of the collapsed stent structure through constant diameter section 206 and into and through lumen of delivery sheath 207.

The device 200 may comprise one or more of the sections to be fit together or it may be manufactured as a unitary device, either embodiment may be fluidly connected with a proximal end of delivery sheath 207.

In addition, a fluid reservoir 208 is provided in operative connection and communication with the at least a portion of the proximal surface of the device. As shown the fluid reservoir 208 comprises a curvilinear shape designed to hold and preserve liquid during the process of loading the stent within the device that will, in turn, preserve the integrity of any biological and/or biologically compatible material integrated with, or attached to, the stent.

The structure of the loading device now explained, the skilled artisan will recognize the utility in effecting transition of a stent from an expanded size to a predetermined collapsed size with a predetermined diameter. Thus, the exemplary stent shown above may be slowly translated through the cylindrical section of constant diameter 202 and along the decreasing diameter section 204. As the stent is advanced, the inner walls of the cylindrical portion 202 and/or the decreasing diameter section 204 exert a force that is circumferentially equal around the stent, thus enabling the stent to collapse along the points of least resistance and least stress. As discussed above, the circular and/or spiral struts will enable a predetermined, predictable and repeatable collapsing motion, leading to a predetermined, predictable and repeatable collapsed shape comprising a diameter and/or collapsed shape that is determined at least in part by the inner diameter of the distal constant diameter section 206. When the stent has been gradually collapsed and ultimately reaches the distal constant diameter section 206, the collapsed stent may be translated therealong, or along a connected delivery sheath or catheter 207 of same or similar inner diameter as the distal constant diameter section 206 to the anatomical location of interest. When the collapsed stent is released from the distal end of the constraining structure, it will be allowed to biasingly expand, effectively reversing the collapsing motion to reach an expanded state or configuration.

Figure 7:
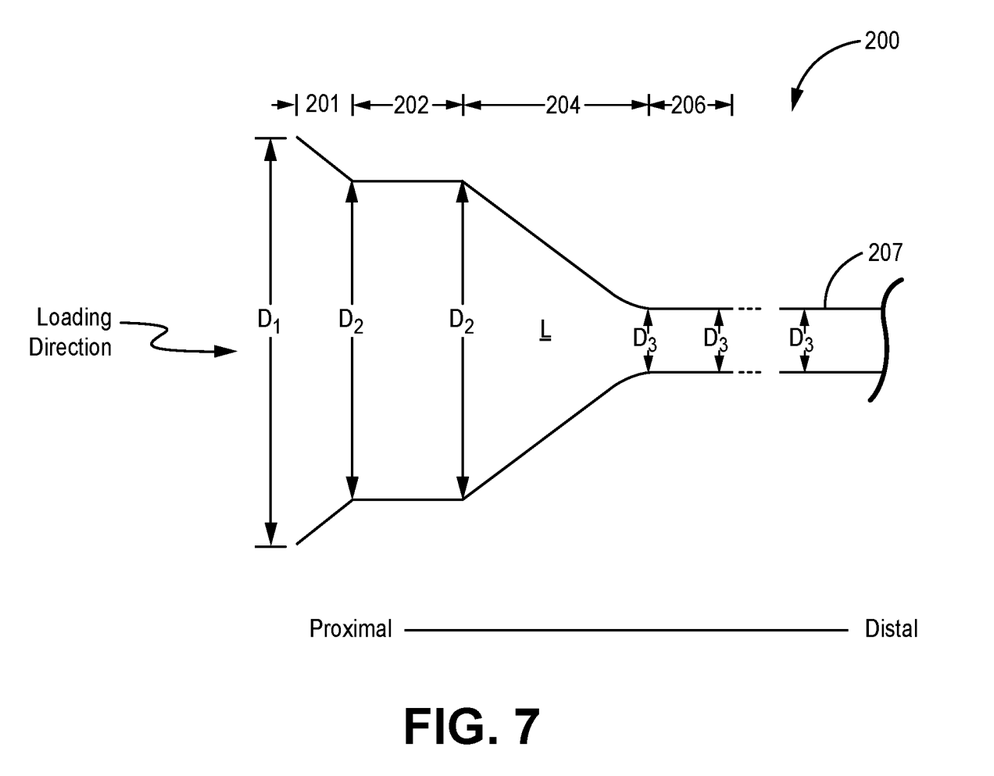
FIG. 7 illustrates a side cross-sectional and cutaway view of one embodiment of the present invention.

Generally, as shown in FIGS. 5, 6 and 7, loading device 200 comprises a lumen L defined therethrough of changing inner diameter. Thus, moving from the proximal to the distal direction, proximal transition section 201 comprises at its proximal end an inner diameter D1 that is the maximum inner diameter of device 200 and which transitions at the distal end of proximal transition section 201 to an inner diameter D2 that is smaller than D1. Distal end of proximal transition section 201 is operatively and fluidly engaged with the proximal end of cylindrical section 202 of constant inner diameter D2 which is the same inner diameter D2 as that of the distal end of proximal transition section 201. Distal end of constant diameter section 202 is operatively and fluidly engaged with the proximal end of decreasing diameter section 204 which comprises an inner diameter D2 at its proximal that is the same as the inner diameter D2 of cylindrical section of constant diameter. Decreasing diameter section 204 defines a decreasing inner diameter along its length from proximal end to distal end where the inner diameter is at a minimum of D3 for the entire lumen L of device 200. Distal constant diameter section 206 is in fluid and operative engagement with the distal end of decreasing diameter section and comprises the same inner diameter D3 as the distal end of decreasing diameter section 204 which is the same inner diameter D3 as the lumen defined by the delivery sheath 207 to which the distal end of distal constant diameter section is operatively and fluidly engaged.

The loading device discussed above, further enables a stent comprising biological or other materials that must be kept moistened to retain the required moisture during loading. In addition, a stent comprising biological or other materials that must be kept moist may be pre-loaded for future use. Thus, a stent may be collapsed and loaded into the loading device's lumen, together with fluid captured by the fluid reservoir 208 to keep the biological and/or biologically compatible material(s) properly wetted in preparation for translation, delivery and implant either immediately after loading or at a later time, i.e., preloading. Fluid reservoir 208 is shown as comprising an inner curved surface 209 and a lip 210 surrounding the top 212 of reservoir 208 and may, in some embodiments as shown, take the form of a cup with an open top. Lip 210 may extend inwardly across a portion of inner curved surface 209 to assist in retaining fluid and/or collapsed or partially collapsed stent within fluid reservoir 208. In practice, biocompatible fluid may be added to the fluid reservoir 208 so that at least a portion of the collapsing and/or collapsed stent structure, e.g., the prosthetic valve leaflets and/or skirt material disposed on outer and/or inner surface of the collapsed stent may be disposed within the fluid.

In some embodiments, the preloading may comprise collapsing the stent at least partially within either the proximal transition section 201 and/or the cylindrical section of constant diameter 202 with continued wetting of critical biological or biocompatible materials associated with the stent by immersion in fluid within fluid reservoir 208. In other cases, preloading may comprise at least partial collapsing of the stent within distal constant diameter section 206 with continued wetting of critical biological or biocompatible materials associated with the stent by immersion within fluid reservoir 208.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A loading device for collapsing a stent comprising material requiring moisture retention in preparation for delivery and implantation into a body, the loading device comprising:
a fluid reservoir comprising a curved inner surface and operatively connected with a proximal end of the loading device and in fluid communication with an inner lumen of the loading device; and a fluid, wherein the fluid reservoir is configured to be at least partially filled with a fluid, wherein the fluid reservoir comprises an open upper surface configured to allow placement of the stent into contact with the fluid.

2. The loading device of claim 1, wherein the fluid is biocompatible.

3. The loading device of claim 1, wherein the fluid reservoir comprises an open cup shape wherein the open upper surface comprises a lip that extends around the open upper surface and extends partially over the curved inner surface of the fluid reservoir.

4. The loading device of claim 1, wherein the stent comprises a prosthetic heart valve frame.

5. The loading device of claim 2, wherein the stent comprises a prosthetic mitral valve frame.

6. The loading device of claim 1, wherein the stent comprises an intravascular stent.

7. The loading device of claim 2, wherein the material requiring moisture retention comprises prosthetic leaflets comprising a biological or biocompatible material and wherein the prosthetic leaflets are immersed within the fluid reservoir.

8. The loading device of claim 1, wherein the inner lumen comprises two regions of decreasing inner diameter moving from a proximal end of the lumen to a distal end of the lumen.

9. The loading device of claim 7, wherein a stent is adapted to be at least partially collapsed within the inner lumen of the loading device, and wherein the material requiring moisture retention is immersed within the fluid of the fluid reservoir.

10. The loading device of claim 7, wherein the inner lumen comprises two sections of constant inner diameter.

11. The loading device of claim 7, wherein the two sections of constant inner diameter are not the same inner diameter.

12. The loading device of claim 10, wherein the distal-most region of constant inner diameter is the minimum inner diameter of the lumen of loading device.

13. A method of loading a stent for collapsing, delivery and implantation within an anatomical target, comprising:
providing a collapsible and expandable stent;
providing a loading device comprising:
a fluid reservoir comprising a curved inner surface, and an open upper surface and operatively connected with a proximal end of the loading device and in fluid communication with an inner lumen of the loading device; and a fluid, wherein the fluid reservoir is configured to be at least partially filled with a fluid, wherein the inner lumen of the loading device comprises two sections of decreasing inner diameter in the proximal-to-distal direction, and two sections of constant inner diameter;
translating the collapsible and expandable stent across the open upper surface and into the inner lumen of the loading device to initiate a controlled, predictable collapsing of the stent within the inner lumen while ensuring that at least a portion of the collapsible and expandable stent is immersed within the fluid of the fluid reservoir; and
applying pressure to further translate the stent through the inner lumen wherein the collapsed stent achieves the predetermined shape and diameter for translation, delivery and implantation; and
applying pressure to further translate the collapsed stent into a lumen of an operatively connected delivery sheath for translation, delivery and implantation.

14. A method of pre-loading a stent to a collapsed configuration in preparation for subsequent translation and implantation within an anatomical target, comprising:
providing a collapsible and expandable stent comprising a material requiring moisture retention;
providing a loading device comprising:
a fluid reservoir comprising a curved inner surface and an open upper surface, and operatively connected with a proximal end of the loading device and in fluid communication with an inner lumen of the loading device; and a fluid, wherein the fluid reservoir is configured to be at least partially filled with a fluid, wherein the inner lumen of the loading device comprises two sections of decreasing inner diameter in the proximal-to-distal direction, and two sections of constant inner diameter;
translating the collapsible and expandable stent across the open upper surface and partially into the inner lumen of the loading device to initiate a controlled, predictable partial collapsing of the stent within the inner lumen while ensuring that at least a portion of the collapsible and expandable stent is immersed within the fluid of the fluid reservoir to wet the material requiring moisture retention; and
subsequently further translating the partially collapsed stent into the inner lumen of the loading device to achieve a predetermined collapsed shape and diameter for translation through a lumen of an operatively connected delivery sheath for translation, delivery and implantation to the anatomical target.

* * * * *